(12) United States Patent
Shah et al.

(10) Patent No.: US 11,940,436 B1
(45) Date of Patent: Mar. 26, 2024

(54) ELECTROANALYTICAL SENSOR FOR MELOXICAM DETECTION

(71) Applicant: United Arab Emirates University, Al Ain (AE)

(72) Inventors: Iltaf Shah, Al Ain (AE); Afzal Shah, Islamabad (PK)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 18/212,467

(22) Filed: Jun. 21, 2023

(51) Int. Cl.
*G01N 33/15* (2006.01)
*G01N 27/30* (2006.01)
*G01N 27/327* (2006.01)

(52) U.S. Cl.
CPC ........... *G01N 33/15* (2013.01); *G01N 27/308* (2013.01); *G01N 27/3278* (2013.01)

(58) Field of Classification Search
CPC ... G01N 33/15; G01N 27/308; G01N 27/3278
See application file for complete search history.

(56) References Cited

FOREIGN PATENT DOCUMENTS

| CN | 105628682 A | * | 6/2016 | ............. | G01N 21/66 |
| CN | 108445060 A | * | 8/2018 | ............. | G01N 27/30 |

OTHER PUBLICATIONS

Cerón-Pérez et al., "Developing a Voltammetric Method for Meloxicam Determination Using a Glassy Carbon Electrode Modified with Multi-walled Carbon Nanotubes (GC/MWCNT)," ECS Transaction, 101 (1), 57-67 (2021) (Year: 2021).*
EPO machine-generated English language translation of Liu et al. CN 108445060 A , patented Aug. 24, 2018 (Year: 2018).*
EPO machine-generated English language translation of Li et al. CN 105628682 A , patented Jun. 1, 2016 (Year: 2016).*
Ibrahim et al., "Newly Developed Nano Sensitive Carbon Paste Electrode Modified with Silver Sulphadiazine and Zinc Oxide for Voltammetric Determination of Loperamide Hydrochloride in Pharmaceutical Formulation and in Human Plasma," Journal of the Electrochemical Society, 2022 169 056507 (Year: 2022).*

* cited by examiner

*Primary Examiner* — Alexander S Noguerola
(74) *Attorney, Agent, or Firm* — MH2 TECHNOLOGY LAW GROUP, LLP

(57) ABSTRACT

The present disclosure discloses an electroanalytical sensor for the detection of meloxicam. The electroanalytical sensor comprises a carbon electrode. The carbon electrode comprises zinc oxide (ZnO) nanoparticles, wherein the ZnO nanoparticles are co-doped with silver (Ag) and cobalt (Co). The present disclosure also discloses a method of detecting meloxicam using an electroanalytical sensor. The electroanalytical sensor comprises a carbon electrode, the carbon electrode comprising zinc oxide (ZnO) nanoparticles co-doped with silver (Ag) and cobalt (Co). The method of detecting meloxicam comprises the step of positioning a liquid droplet, comprising solvent, to be tested on a surface of the electrode. The method further comprises receiving a voltammetric response from the electrode, and analysing the voltammetric response to determine if meloxicam is present in the liquid droplet.

18 Claims, 2 Drawing Sheets

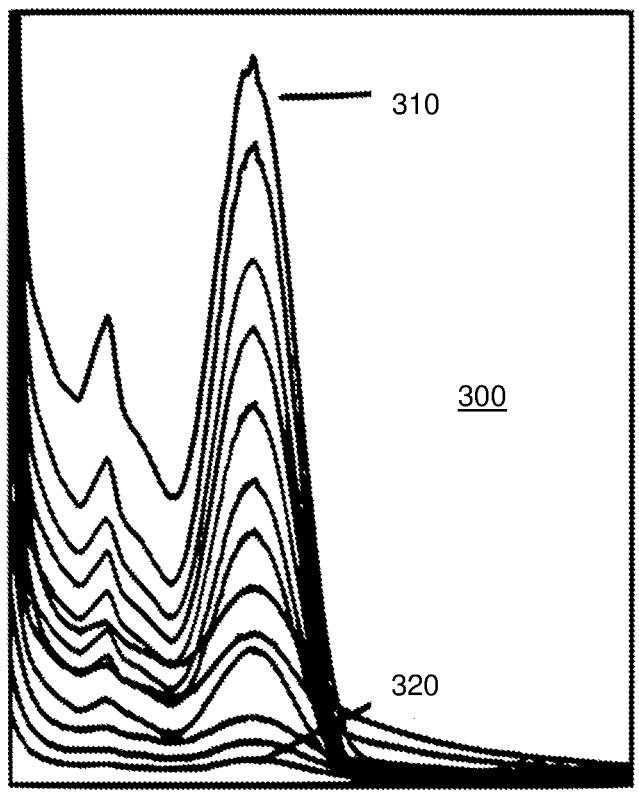
Fig. 3
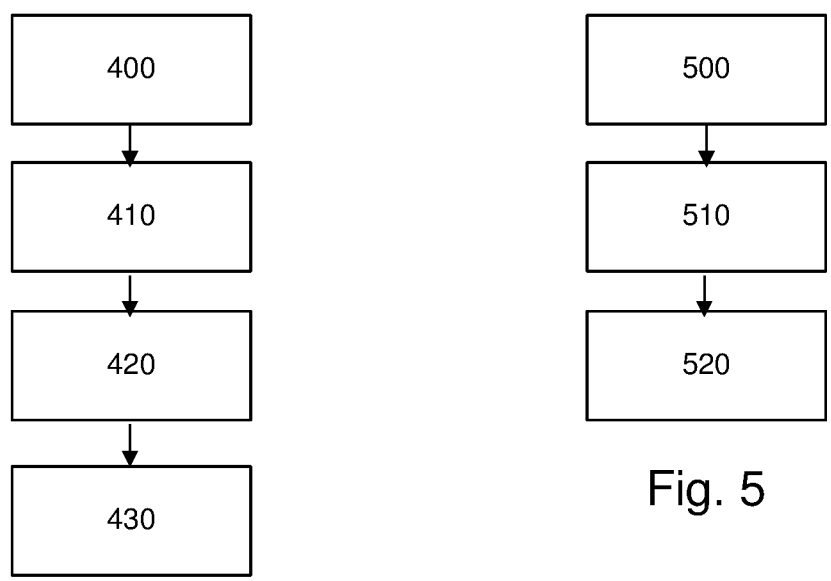
Fig. 4
Fig. 5

ELECTROANALYTICAL SENSOR FOR MELOXICAM DETECTION

TECHNICAL FIELD

The present disclosure concerns electroanalytical sensors. More particularly, but not exclusively, the present disclosure concerns electroanalytical sensors for the detection of meloxicam.

BACKGROUND

Background description includes information that will be useful in understanding the present invention. It is not an admission that any of the information provided herein is prior art or relevant to the presently claimed invention, or that any publication specifically or implicitly referenced is prior art.

Pharmaceutical drugs are used for the prevention and treatment of diseases. Meloxicam is a strong prescription drug, often prescribed as a potent painkiller.

However, meloxicam can cause a number of side-effects, such as high blood pressure, bleeding, ulcers, holes in intestines, yellowing of the skin or whites of the eyes, liver inflammation, breathing difficulty, and allergic reactions. The Food and Drug Administration (FDA) has issued heart, stomach, and intestine black box warnings about the dangerous side effects of meloxicam.

After excretion from the patient, meloxicam and its metabolites can find its way into water bodies such as water reservoirs. Meloxicam can also enter water bodies through improper handling, particularly by pharmaceutical companies.

For example, the effluents discharged into water bodies from pharmaceutical companies may contain drugs (including meloxicam) and their metabolites. In regions where drug disposal regulations are more lax, or where they are not enforced or adhered to sufficiently, waste drugs (including meloxicam) make their way into water bodies.

The consequence of this is that meloxicam and its metabolites pollute water and pose a health risk to not only humans, but other flora and fauna. Consumption and absorption of meloxicam by aquatic creatures can also pose a threat to human health. Therefore, the detection and monitoring of meloxicam in water bodies is important for human, animal, and plant health.

Therefore, it is important to be able to detect meloxicam and obtain a profile of meloxicam and its metabolites.

A variety of standard analytical methods for drug monitoring are large, and bulky. These devices require large sample sizes and take a long time to perform the analysis.

Existing electroanalytical methods have poor electrocatalytic properties, and have poor peak current for meloxicam detection, as well as issues with interference from other pharmaceutical compounds.

Therefore, a sensitive and selective analytical sensor is highly required for its minute-level detection.

The present disclosure seeks to mitigate the above-mentioned problems. Alternatively, or additionally, the present disclosure seeks to provide an improved sensor for the detection of meloxicam.

SUMMARY

The present disclosure provides, according to a first aspect, an electroanalytical sensor for the detection of meloxicam, the electroanalytical sensor comprising a carbon electrode, the carbon electrode comprising zinc oxide (ZnO) nanoparticles, wherein the ZnO nanoparticles are co-doped with silver (Ag) and cobalt (Co).

Electroanalytical sensors can be calibrated such that the voltammetric responses received from the sensor are highly specific and selective based on the analyte being detected. Electroanalytical sensors of the present disclosure are able to discriminate the voltammetric response of meloxicam even in the presence of interfering agents that are higher in concentration by many multiples. Electroanalytical sensors of the present disclosure also enable the possibility of real-time results.

Zinc oxide (ZnO) nanoparticles advantageously improve the photocatalytic properties of the sensor, particularly for the degradation of meloxicam.

The inventors surprisingly found that ZnO nanoparticles that are co-doped with silver (Ag) and cobalt (Co) have further advantageous effects. Ag and Co synergistically with the ZnO nanoparticles has an electrocatalytic performance that can be up to several orders of magnitude over conventional means. The synergistic effect of the co-dopants has led to band gap tuning, band reduction, and enhanced the electrocatalytic and photocatalytic role of ZnO, which results in an intense peak current of meloxicam and its efficient photocatalytic degradation.

Additionally, the synthesised catalyst is more environmentally positive as it is environmentally benign and therefore does not cause secondary pollution. The catalyst can also be recovered and re-used up to three times. When re-used, the catalyst may experience an efficiency loss of less than 3%.

In testing, the inventors found that when meloxicam was photocatalytically degraded, and the photocatalytic degradation was monitored spectrophotometrically as well as at the designed nano sensor, the extent and kinetics of meloxicam degradation results were found in agreement. This demonstrates that the sensor and/or the method(s) of the present disclosure can accurately detect meloxicam and treat wastewater contaminated with meloxicam.

The carbon electrode may comprise a surface. The surface may be an upper surface. The surface, or upper surface, may be modified with the ZnO nanoparticles co-doped with silver and cobalt.

The silver and cobalt may be co-doped at substantially 2%. Substantially 2% may refer to a range between 1.5% and 2.5%. This percentage range enhances the light absorption capacity and conductivity of the ZnO.

The electroanalytical sensor may be a nano sensor. Nano sensors are smaller than conventional sensors, and consequently require less analyte in order to detect the presence of the compound being tested for.

The carbon electrode may be a glassy carbon electrode. The carbon electrode may comprise carbon nanotubes. The carbon nanotubes may be multiwalled carbon nanotubes. The multiwalled carbon nanotubes may be carboxyl functionalised carbon nanotubes. The term carboxyl may refer to carboxylic acid.

The surface, or upper surface, may be modified with carbon nanotubes. The surface, or upper surface, may be modified with multiwalled carbon nanotubes. The surface, or upper surface, may be modified with carboxyl functionalised multiwalled carbon nanotubes.

The surface, or upper surface, comprising, or being modified with, carbon nanotubes and/or ZnO nanoparticles may not be mutually exclusive.

The addition of carbon nanotubes to the carbon electrode enhances the electrical properties of the electrode. Additionally, the synergistic effect of the co-doped ZnO nanoparticles and the carbon nanotubes enhances the electrochemical response of the meloxicam at the electrode surface.

The modified glassy carbon electrode may have an electroanalytical signal that is enhanced by 11 times compared to the electroanalytical signal of an unmodified glassy carbon electrode. The signal may also be shifted to less positive potentials, indicating facile oxidation of meloxicam.

According to a second aspect of the present disclosure, there is provided a method of detecting meloxicam using an electroanalytical sensor, the electroanalytical sensor comprising a carbon electrode, the carbon electrode comprising zinc oxide (ZnO) nanoparticles co-doped with silver (Ag) and cobalt (Co). The method of detecting meloxicam comprises the steps of: positioning a liquid droplet, comprising solvent and analyte, to be tested on a surface of the electrode; receiving a voltammetric response from the electrode; and analysing the voltammetric response to determine if meloxicam is present in the liquid droplet.

The method of detecting meloxicam may comprise the step of evaporating the solvent of the liquid droplet such that the analyte remains on the surface of the electrode as a dry residue.

The inventors surprisingly found that by evaporating the solvent from the liquid droplet and leaving behind a dry residue, the diffusion step in conventional electroanalytical methods is bypassed. The diffusion step in conventional methods is often the step that limits the rate at which the analysis can be conducted. By evaporating the solvent from the liquid drop, the speed at which analysis can be conducted is increased. Furthermore, time lag in the diffusion of solvated analyte molecules is substantially eliminated, which results in the production of a voltammetric response with sharper peaks, which is more desirable for quantitative analysis. By drying the liquid drop, dried analyte molecules have much better accessibility to the electrode surface leading to more efficient electron transfer and a much sharper peak.

The time to respond to an analyte may be 20 seconds or less. The method of the present disclosure allows for faster detection time of meloxicam. The time to respond to an analyte may be 15 seconds or less. The time to respond to an analyte may refer to the time to produce a voltammetric response that corresponds to the presence of meloxicam. The time to respond to an analyte may be 10 seconds or less.

The method of detecting meloxicam may comprise the step of dipping the electrode in an electrolyte solution.

The method of detecting meloxicam wherein the electrolyte solution may comprise one of hydrochloric acid, potassium chloride, potassium nitrate, sulfuric acid, sodium chloride, sodium hydroxide, phosphate-buffered saline, or Britten Robinson buffer.

The electrolyte solution may comprise Britten Robinson buffer.

The options for use in the electrolyte solution have been found to improve the current response of the target analyte meloxicam. The use of Britten Robinson as a buffer has been found to provide the highest peak current response of the target analyte meloxicam.

The electrolyte solution may have a pH within the range of 1 to 10.

The electrolyte solution may have a pH within the range of 3.5 to 4.5.

The electrolyte solution may have a pH of substantially about 4.

The chosen pH ranges, and in particular a pH of around 4 (within the range of between 3.5 to 4.5), has been found to provide the best medium for rapid electron transfer of the meloxicam.

The method of detecting meloxicam wherein the electroanalytical sensor may be a nano sensor.

The method of detecting meloxicam wherein the carbon electrode may be a glassy carbon electrode.

The method of detecting meloxicam, wherein the droplet may be less than 10 microlitres in volume. The features of the present disclosure result in the ability to use a droplet size that is much smaller than what is conventionally required. The droplet may be less than 9 microlitres, or less than 8 microlitres, or less than 6 microlitres, or less than 5 microlitres in volume.

The method of detecting meloxicam, wherein the electrode further comprises carboxyl functionalized multiwalled carbon nanotubes. The inclusion of carboxyl functionalised multiwalled carbon nanotubes enhances the electrical characteristics of the electrode.

According to an aspect of the present disclosure there is provided a method of monitoring the degradation rate of meloxicam, the method comprising the method according to the second aspect, wherein the step of analysing the voltammetric response comprises analysing the voltammetric response over a predetermined time period, such that a degradation profile over the predetermined time period is obtained.

A method of monitoring the degradation rate of meloxicam, wherein the predetermined time period may be 60 minutes or less. Features of the present disclosure enable a quicker analysis time compared to the prior art. A full degradation profile may be obtained in 60 minutes or less. The predetermined time period may be 55 minutes or less, or 50 minutes or less, or 45 minutes or less, or 40 minutes or less, or 35 minutes or less, or 30 minutes or less.

It will of course be appreciated that features disclosed in relation to one aspect may be used in combination with another aspect, and vice versa.

BRIEF DESCRIPTION OF THE DRAWINGS

The manner in which the above-recited features of the present invention is understood in detail, a more particular description of the invention, briefly summarized above, may be had by reference to embodiments, some of which are illustrated in the appended drawings. It is to be noted, however, that the appended drawings illustrate only typical embodiments of the present disclosure and are therefore not to be considered limiting of its scope, for the present disclosure may admit to other equally effective embodiments.

FIG. 3 shows a voltammetric response according to an embodiment of the present disclosure.

FIG. 4 shows a method of detecting meloxicam according to an embodiment of the present disclosure.

FIG. 5 shows a method of monitoring the degradation rate of meloxicam according to an embodiment of the present disclosure.

The foregoing and other objects, features and advantages of the present invention, as well as the invention itself, will be more fully understood from the following description of preferred embodiments, when read together with the accompanying drawings.

DETAILED DESCRIPTION

The present disclosure relates to the field of electroanalytical sensors, and more particularly to electroanalytical nano sensors for the detection of meloxicam.

The principles of the present invention and their advantages are best understood by referring to the embodiments disclosed in FIG. 1 to FIG. 5. In the following detailed description of illustrative or exemplary embodiments of the disclosure, specific embodiments in which the disclosure may be practiced are described in sufficient detail to enable those skilled in the art to practice the disclosed embodiments. The following detailed description is, therefore, not to be taken in a limiting sense, and the scope of the present disclosure is defined by the appended claims and equivalents thereof.

References within the specification to "one embodiment," "an embodiment," "embodiments," or "one or more embodiments" are intended to indicate that a particular feature, structure, or characteristic described in connection with the embodiment is included in at least one embodiment of the present disclosure.

Figure 1:
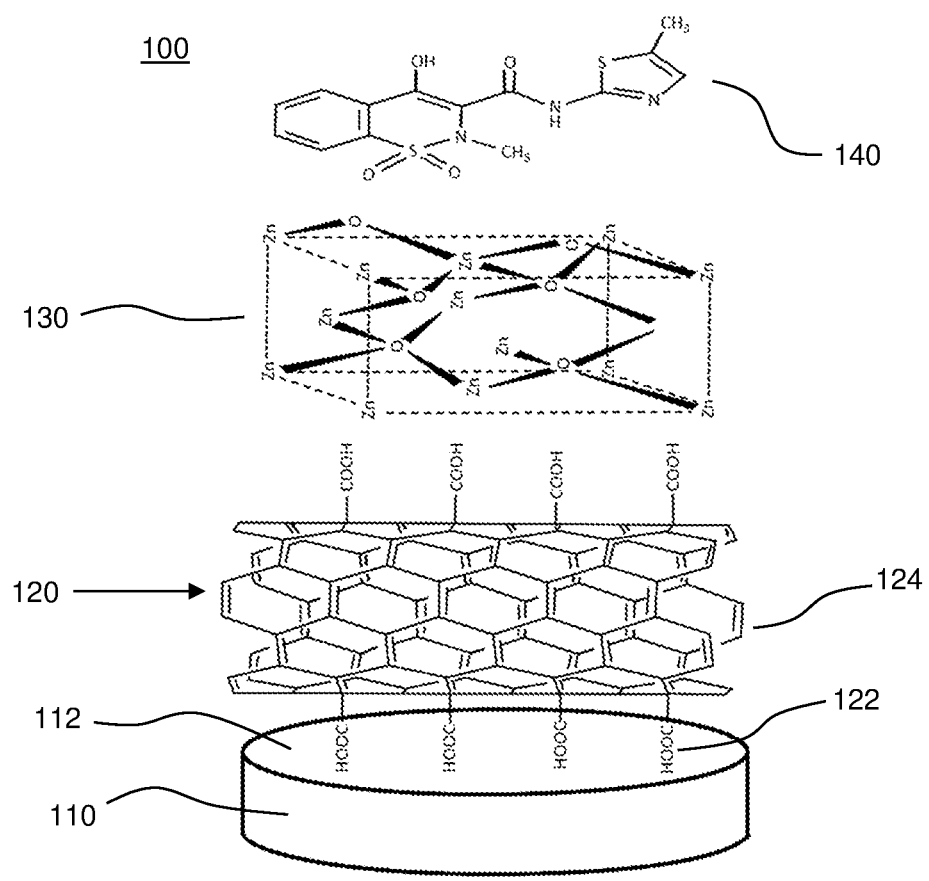
FIG. 1 shows an electroanalytical nano sensor according to an embodiment of the present disclosure.

FIG. 1 shows an electroanalytical nano sensor 100. The electroanalytical nano sensor 100 comprises a glassy carbon electrode 110. The electrode 110 has an upper surface 112 that is modified with carbon nanotubes 120. The carbon nanotubes 120 are carboxyl functionalised multiwalled carbon nanotubes 120 (COOH-fMWCNTs). The nanotubes 120 comprise multiwalled carbon nanotubes 124 and carboxyl groups 122. The carboxyl groups 122 are carboxylic acid groups 122.

The modification of the electrode 110 with the COOH-fMWCNTs 120 imparts conductivity characteristics to the electrode 110 and enhances its electrical properties.

The electrode 110 is further modified with zinc oxide (ZnO) co-doped with silver (Ag) and Cobalt (Co) (Ag—Co—ZnO) 130. ZnO is an n-type semiconductor with a wide band gap that allows it to primarily absorb ultraviolet radiations. Its band gap can be tuned via doping and co-doping.

The Ag—Co—ZnO 130 has multiple benefits for the detection of meloxicam, such as enhancing the surface area of the electrode surface, and enhancing the electrocatalytic roles. This results in faster detection time of meloxicam.

Additionally, the combination of the functional groups in the electrode modifier facilitates the host-guest complexation leading to enhanced signals of the target analytes. Moreover, the electrode surface is modified to achieve improved conductivity, porosity, greater surface area and active site enhancement for better sensing of the target analyte.

Meloxicam 140 is found to degrade by up to 16% in two hours in the presence of sunlight without catalyst. The degradation increased to 90% within one hour when ZnO and Ag—Co—ZnO were used as photocatalysts. The degradation rate further increased when Fenton's reagent was used along with Ag—Co—ZnO, leading to a 98% degradation in 48 minutes. This demonstrates that the sensor according to embodiments of the present disclosure is suitable for serving two purposes: sensing the presence of meloxicam; and measuring its photocatalytic degradation.

It is found that using a sensor according to embodiments of the present disclosure, a response to analyte may be received in under a second, while the most intense signal may be received in under 20 seconds. In embodiments, the most intense signal may be received in under 15 seconds.

Additionally, according to embodiments, the sensor is more environmentally friendly and uses biocompatible electrode modifiers. The World Health Organization has formalized the ASSURED criteria as a benchmark for sensing analytics to produce a robust sensing platform for real-time monitoring. A scaffold with Ag—Co—ZnO (130) and COOH-fMWCNTs (120) as modifiers of the electrode surface for the detection of meloxicam and real-time monitoring of its metabolites is more environmentally friendly than conventional sensors.

In embodiments, there is provided a method of synthesising an electroanalytical nano sensor as depicted in FIG. 1. The synthesis may comprise the use of biological components (phytochemicals) in in lemon peel extract as a reducing and capping agent. Therefore, no additional capping and reducing agent is needed to be added to the reaction mixture. Lemon peel extract contributes to the environmentally/ecologically friendly synthesis approach of embodiments of the present disclosure.

The approach also consumed less energy, further adding to the environmental credentials of the device/method. Plant mediated synthesis of components reduces the toxicity of nanomaterials, provides high stability, achieves degradation of pharmaceutical waste without the production of secondary pollutants, and can be used for the large scale production of nanoparticles.

Figure 2:
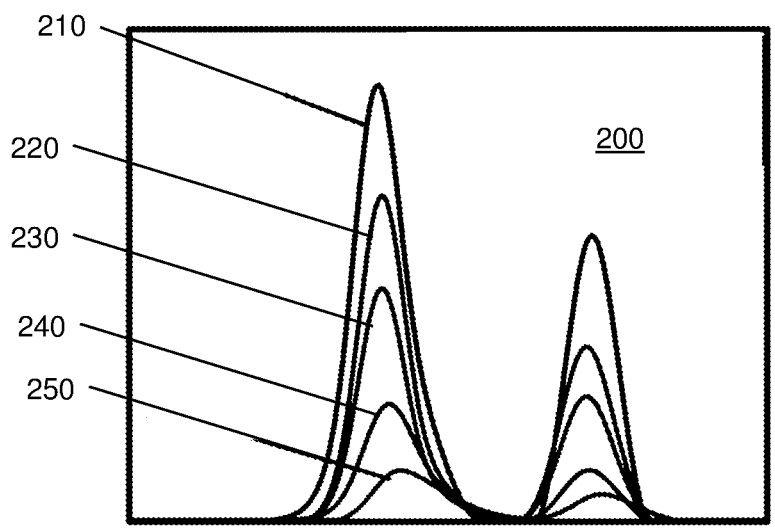
FIG. 2 shows a voltammetric response according to an embodiment of the present disclosure.

FIG. 2 shows a series of voltammetric responses 200 according to an embodiment of the present disclosure. Each of the peaks shown depict a response to the presence of meloxicam using different modifications of a glassy carbon electrode (GCE).

The term voltammetric response is a term of the art, and may also be referred to by the terms electrochemical signal, oxidation signal, or electro-oxidation response.

The weakest response is produced by bare GCEs 250. The response peak is increased by the addition of COOH-fMWCNTs and Ag—Co—ZnO to the GCE, resulting in the sharpest peak 210.

The peak 220 refers to the response corresponding to a GCE modified with COOH-fMWCNTs. The peak 230 refers to the response corresponding to a GCE modified with Ag—Co co-doped ZnO. The peak 240 refers to the response corresponding to a GCE modified with ZnO.

FIG. 3 shows a series of voltammetric responses 300 according to an embodiment of the present disclosure. The series 300 shows the decrease in the signal peak with the passage of time. The sharpest peak 310 shows the voltammetric response at time t=0. As time passes, the response decreases. The lowest peak 320 shows the voltammetric response at time t=48 minutes. This corresponds to a 98% degradation of meloxicam.

Embodiments of the present disclosure are suitable for the photocatalytic degradation of meloxicam at rates significantly higher than those of conventional means, and significantly higher than the natural, non-catalysed, degradation rate of meloxicam in sunlight. The series 300 demonstrates that embodiments are also suitable for monitoring the degradation of meloxicam via photo-catalysis. The series 300 also demonstrates that embodiments are also suitable for monitoring the degradation of meloxicam that is non-catalysed.

FIG. 4 shows the method of detecting meloxicam according to an embodiment of the present disclosure. The method of FIG. 4 uses the sensor according to the embodiment of FIG. 1.

Step 400 is the step where a liquid droplet comprising solvent to be tested is positioned on the upper surface of the electrode. In embodiments, the liquid droplet also comprises solute.

In embodiments, the liquid droplet is a 10 microlitre droplet. In embodiments, the liquid droplet is a 10 microlitre droplet of at least 50 micromolar solution of meloxicam.

Step 410 is the step where the solvent of the liquid droplet is evaporated. The evaporation of the solvent leaves behind solute residue on the surface of the electrode.

In step 420, the electrode with the dry solute is dipped into an electrolyte solution.

In step 430, the voltammetric response is analysed to determine if meloxicam is present in the liquid droplet.

In embodiments, the voltammetric response that signifies the presence of meloxicam may be characterised by two peaks. In embodiments, the peaks are adjacent. In embodiments, the first peak is greater than the second peak.

This approach results in the enhancement of the electrochemical signal as molecules of the meloxicam are already present on the electrode surface in a dried form, and their diffusion from the solution is not required. Hence, the diffusion step is circumvented, this diffusion step being a reason for the slower response of conventional electrochemical methods. Current electrochemical methods produce voltammetric responses of analytes with broader peaks due to time lag in the diffusion of solvated analyte molecules from solution and their poor accessibility to the electrode surface, while the method of embodiments of the present disclosure generates an intense signal of the target analyte at least partially due to skipping of the diffusional step through the solution and much closer access to the electrode surface leading to efficient electron transfer and consequent sharp peak as desired for quantitative analysis. Moreover, conventional methods utilize large quantities of samples for investigation in the electrochemical cell. The method of embodiments of the present disclosure demands only a droplet of the sample for analysis and utilizes an electrochemical cell just for solvent in which a modified electrode with the dried sample from the droplet is dipped. Hence, methods according to embodiments are economical, faster, and suitable for quantitative analysis along with the additional benefit of being environmentally friendly.

FIG. 5 shows a method of monitoring the degradation rate of meloxicam according to an embodiment of the present disclosure.

Step 500 is the preparation step for the electrode. Step 500 comprises positioning a liquid droplet that comprises solvent on the upper surface of the electrode. Step 500 further comprises drying the liquid droplet such that a dry residue of solute remains on the surface of the electrode.

In step 510, the electrode is dipped into electrolyte solution.

In step 520, voltammetric response is analysed. The voltammetric response is analysed over a predetermined time period. By analysing the voltammetric response over a predetermined time period, a degradation profile over the time period may be obtained.

In embodiments, the predetermined time period is 60 minutes or less.

In embodiments, Fenton's reagent is used to accelerate the degradation rate of meloxicam, resulting in faster analysis.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents. The disclosures and the description herein are intended to be illustrative and are not in any sense limiting the present disclosure, defined in scope by the following claims.

Many changes, modifications, variations and other uses and applications of the present disclosure will become apparent to those skilled in the art after considering this specification and the accompanying drawings, which disclose the preferred embodiments thereof. All such changes, modifications, variations and other uses and applications, which do not depart from the spirit and scope of the present disclosure, are deemed to be covered by the invention, which is to be limited only by the claims which follow.

The invention claimed is:

1. An electroanalytical sensor for the detection of meloxicam, the electroanalytical sensor comprising:
   a carbon electrode, the carbon electrode comprising zinc oxide (ZnO) nanoparticles,
   wherein the ZnO nanoparticles are co-doped with silver (Ag) and cobalt (Co).

2. An electroanalytical sensor as claimed in claim 1, wherein the carbon electrode is a glassy carbon electrode.

3. An electroanalytical sensor as claimed in claim 1, wherein the electrode further comprises carbon nanotubes.

4. An electroanalytical sensor as claimed in claim 3, wherein the carbon nanotubes are multiwalled carbon nanotubes.

5. An electroanalytical sensor as claimed in claim 4, wherein the multiwalled carbon nanotubes are carboxyl functionalised multiwalled carbon nanotubes.

6. A method of detecting meloxicam using an electroanalytical sensor, the electroanalytical sensor comprising a carbon electrode, the carbon electrode comprising zinc oxide (ZnO) nanoparticles co-doped with silver (Ag) and cobalt (Co), the method of detecting meloxicam comprising the steps of:
   positioning a liquid droplet, comprising solvent and analyte, to be tested on a surface of the electrode;
   receiving a voltammetric response from the electrode; and
   analysing the voltammetric response to determine if meloxicam is present in the liquid droplet.

7. A method as claimed in claim 6, wherein the method comprises the step of:
   evaporating the solvent of the liquid droplet such that the analyte remains on the surface of the electrode as a dry residue.

8. A method as claimed in claim 7, wherein the droplet is less than 10 microlitres in volume.

9. A method as claimed in claim 7, wherein the method comprises the step of dipping the electrode in an electrolyte solution.

10. A method as claimed in claim 9, wherein the electrolyte solution has a pH within the range of 1 to 10.

11. A method as claimed in claim 10, wherein the electrolyte solution has a pH within the range of 3.5 to 4.5.

12. A method as claimed in claim 9, wherein the electrolyte solution comprises one of hydrochloric acid, potassium chloride, potassium nitrate, sulfuric acid, sodium chloride, sodium hydroxide, phosphate-buffered saline, or Britten Robinson buffer.

13. A method as claimed in claim 12, wherein the electrolyte solution comprises Britten Robinson buffer.

14. A method as claimed in claim 6, wherein the carbon electrode is a glassy carbon electrode.

15. A method as claimed in claim 6, wherein the droplet is less than 10 microlitres in volume.

16. A method as claimed in claim 6, wherein the electrode further comprises carboxyl functionalised multiwalled carbon nanotubes.

17. A method of monitoring the degradation rate of meloxicam, the method comprising the method as claimed in claim 6, wherein the step of analysing the voltammetric response comprises analysing the voltammetric response over a predetermined time period, such that a degradation profile over the predetermined time period is obtained.

18. A method as claimed in claim 17, wherein the predetermined time period is 60 minutes or less.

\* \* \* \* \*